(12) United States Patent
von Schuckmann

(10) Patent No.: US 6,508,380 B1
(45) Date of Patent: Jan. 21, 2003

(54) DISPENSER FOR THE DISPENSING ELEMENTS IN STRIPS

(76) Inventor: Alfred von Schuckmann, Winnekendonker Strasse 52, Kevelaer D-47627 (DE)

( * ) Notice: Subject to any disclaimer, the term of this patent is extended or adjusted under 35 U.S.C. 154(b) by 0 days.

(21) Appl. No.: 09/913,839

(22) Filed: Aug. 15, 2001

(30) Foreign Application Priority Data

Dec. 23, 1999 (DE) .......................................... 199 62 305
May 25, 2000 (DE) .......................................... 100 25 886

(51) Int. Cl.$^7$ .............................. B65H 1/08; B65G 59/00
(52) U.S. Cl. ............................... 221/4; 221/6; 221/155; 221/232; 221/255; 221/249; 221/272; 221/274; 271/128
(58) Field of Search ........................... 206/39.4; 221/4, 221/6, 155, 135, 232, 255, 247, 248, 249, 268, 272, 274; 271/42, 128

(56) References Cited

U.S. PATENT DOCUMENTS

| 1,198,394 A | * | 9/1916 | Lilly | 221/232 |
|---|---|---|---|---|
| 1,513,081 A | * | 10/1924 | Album | 221/249 |
| 1,741,295 A | * | 12/1929 | Haberer | 221/232 |
| 2,591,855 A | * | 4/1952 | Nicholson | 221/232 |
| 2,641,358 A | * | 6/1953 | Santo | 221/232 |
| 2,653,704 A | * | 9/1953 | Nelson | 221/232 |
| 3,308,989 A | * | 3/1967 | Alltop et al. | 221/232 |
| 4,171,753 A | * | 10/1979 | Vreede | 221/247 |
| 4,471,885 A | * | 9/1984 | Mucciarone | 221/155 |
| 4,709,912 A | * | 12/1987 | Stuttgart et al. | 221/268 |
| 5,649,642 A | * | 7/1997 | Mabry et al. | 221/232 |

FOREIGN PATENT DOCUMENTS

| DE | 4205805 | 9/1993 |
|---|---|---|
| FR | 2629061 | 9/1989 |
| GB | 605566 | 7/1948 |

* cited by examiner

Primary Examiner—H. Grant Skaggs
(74) Attorney, Agent, or Firm—Martin A. Farber

(57) ABSTRACT

A dispenser (1) for dispensing strip elements (4), having a supply chamber (3) for accommodating a strip-element stack (St), and having a discharging pusher (14) with a nose (16) for interacting with a first strip element (4') of the strip-element stack (St), via a discharging slot (15) which is adapted to the thickness (y) of a strip element (4). In order to achieve a more functionally advantageous solution, the discharging pusher (14) has a pusher nose (16) which is made of elastically compliant material and, in the uninfluenced state, projects by more than the thickness (y) of the strip element (4).

27 Claims, 13 Drawing Sheets

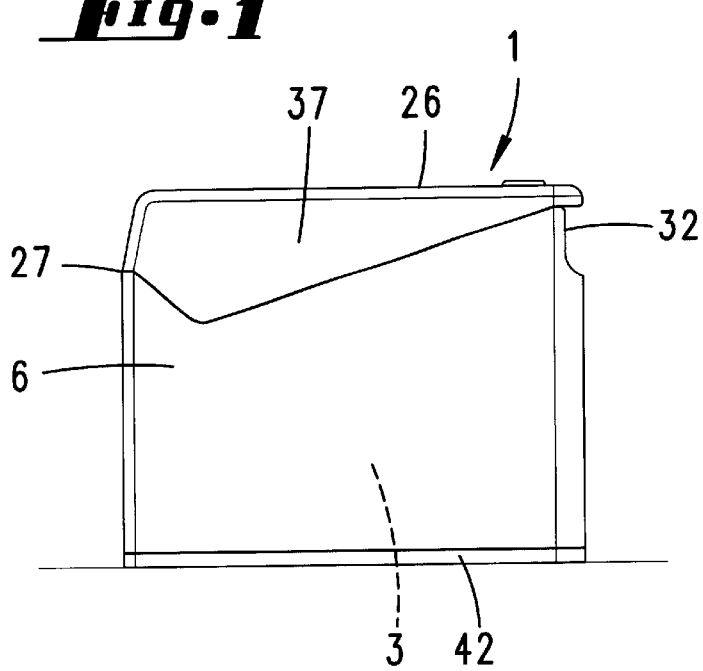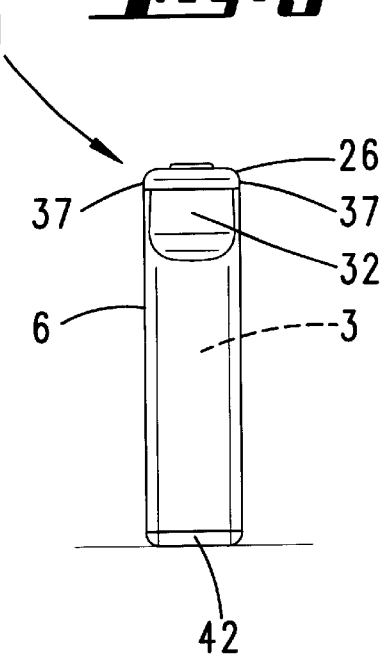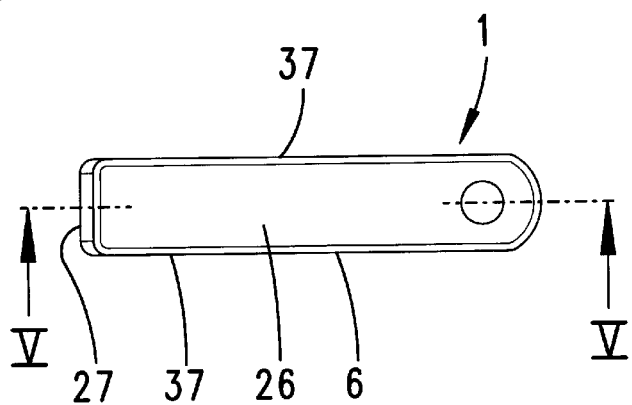

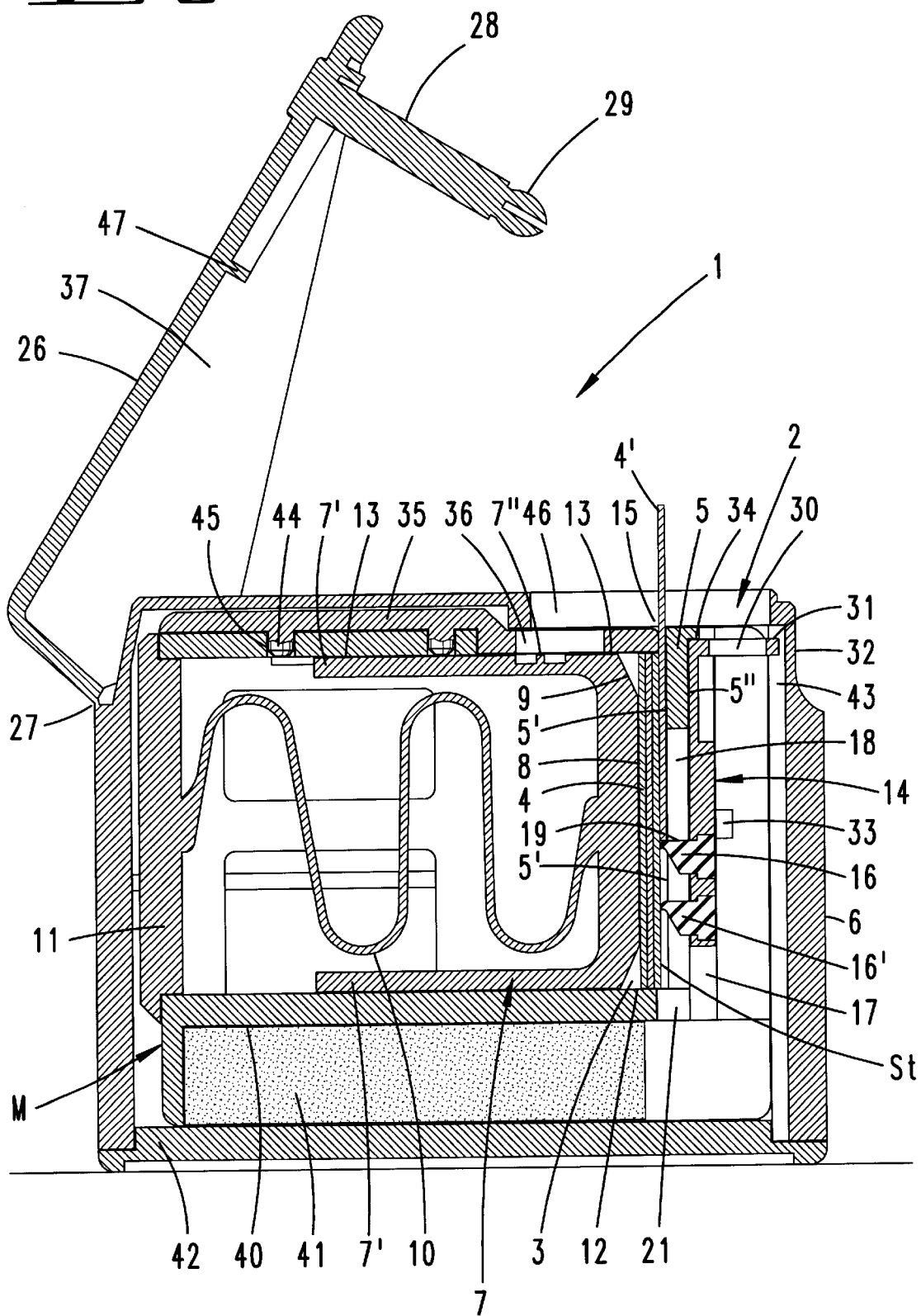

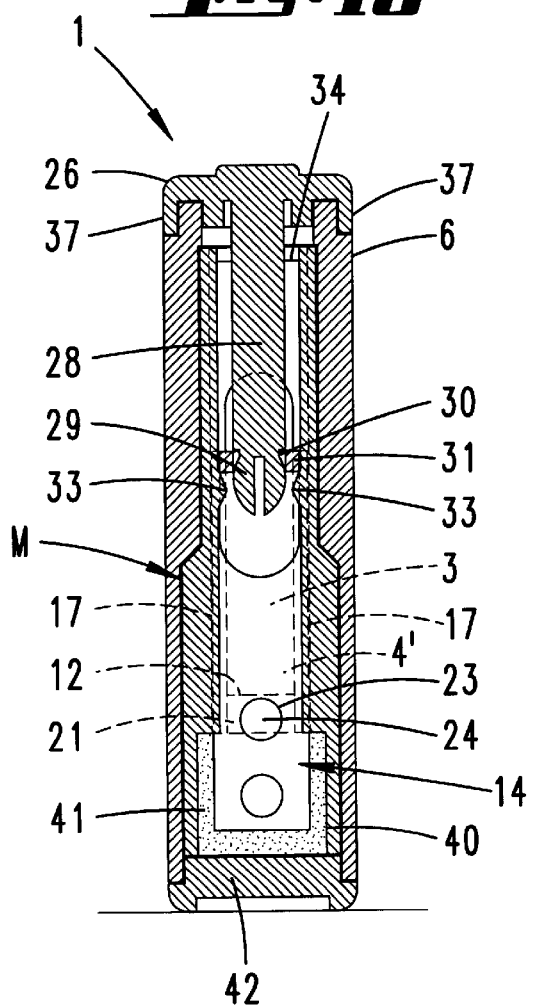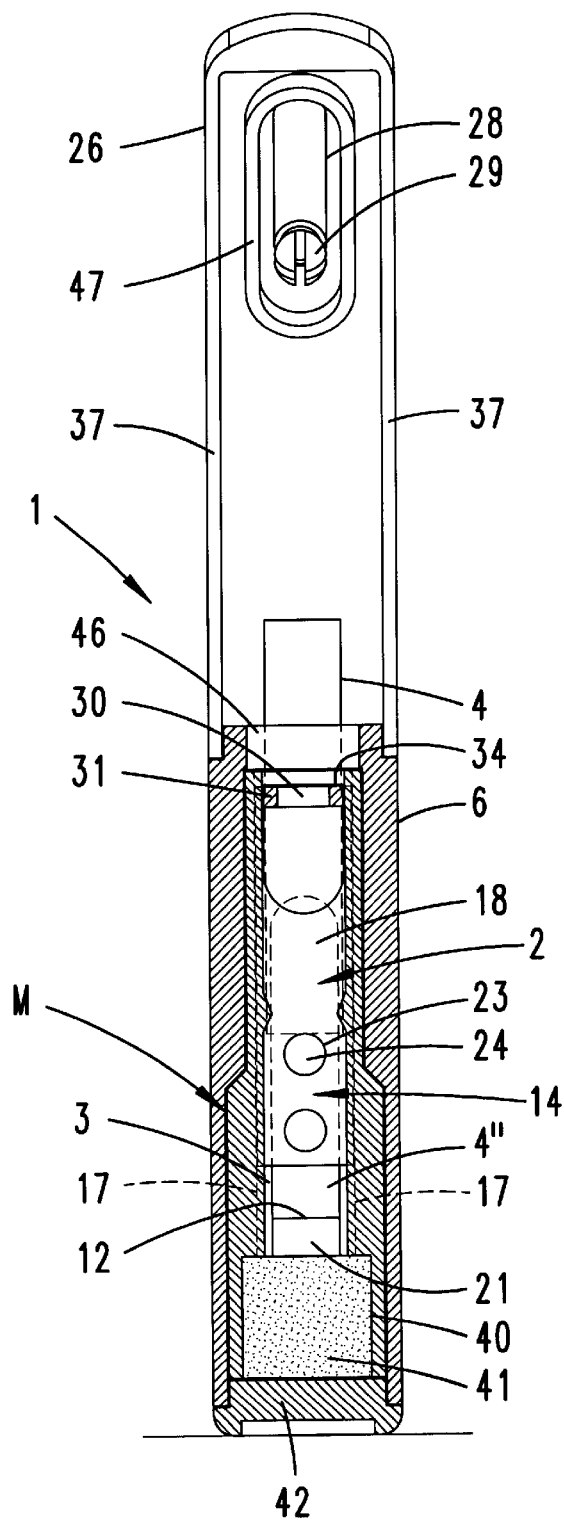

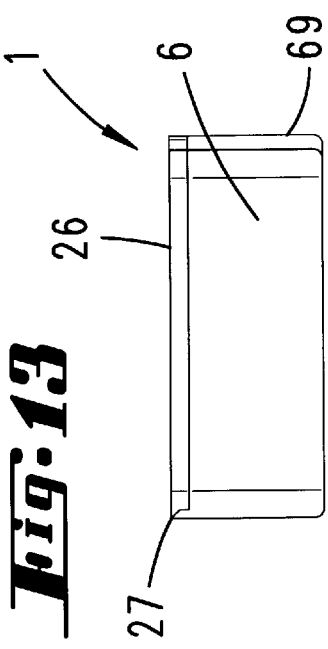
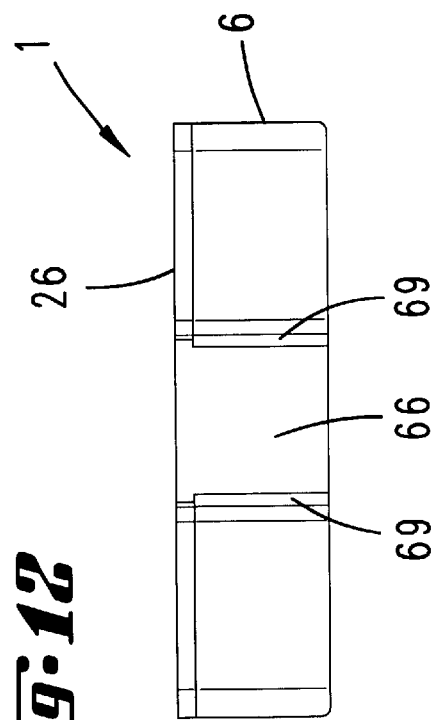
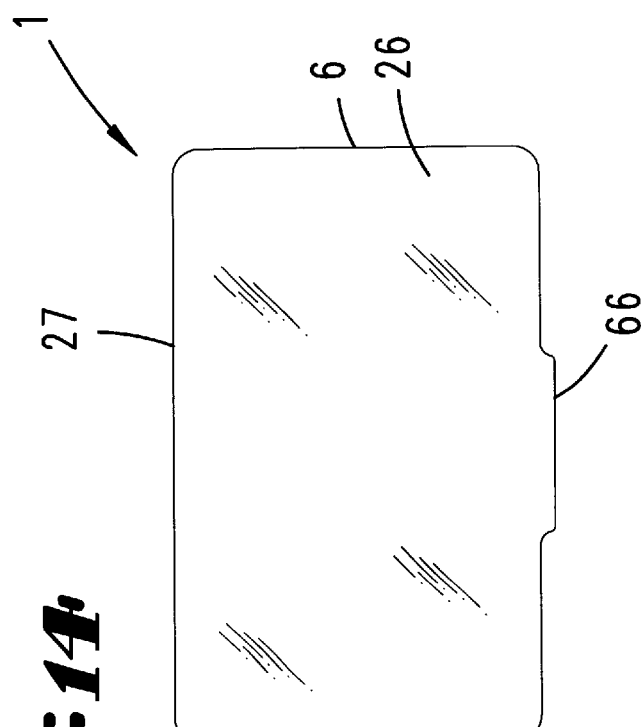

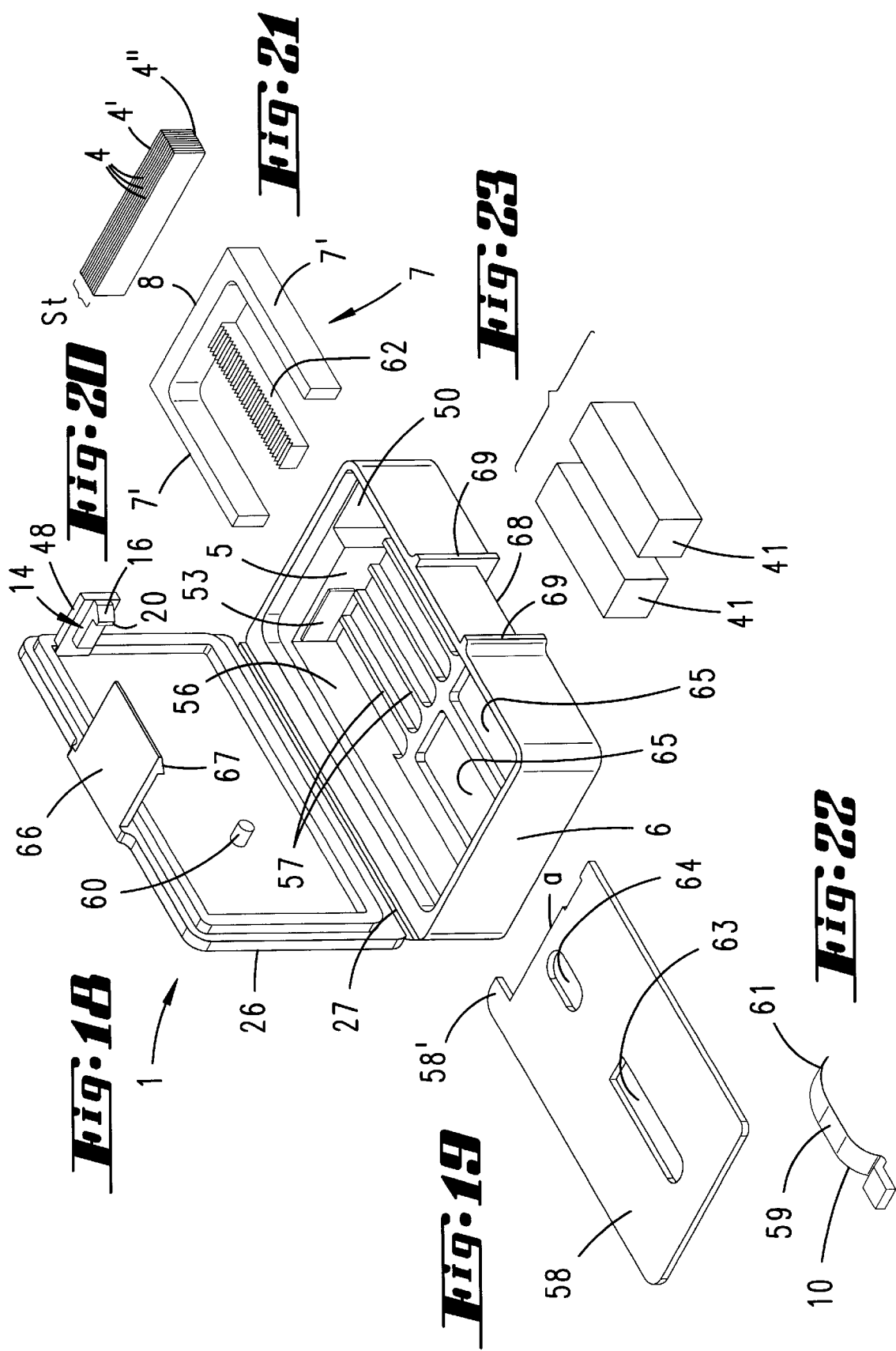

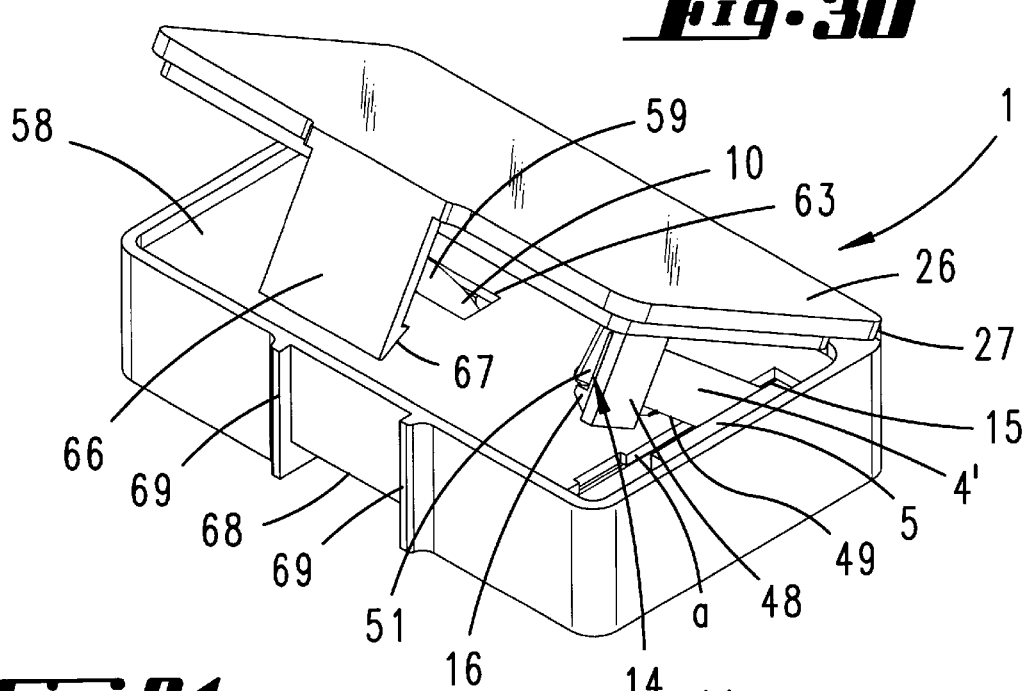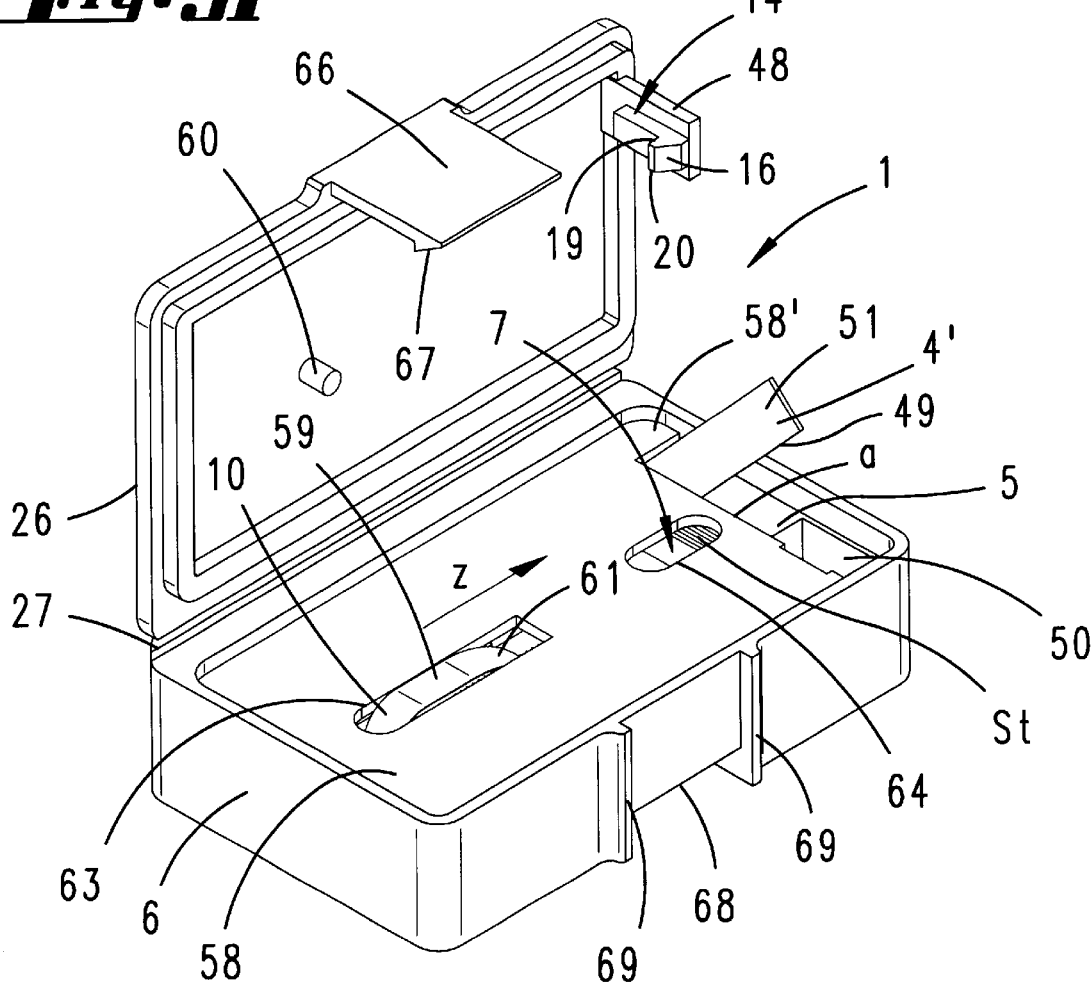

DISPENSER FOR THE DISPENSING ELEMENTS IN STRIPS

A FIELD AND BACKGROUND OF THE INVENTION

The invention relates to a dispenser for dispensing strip elements, having a supply chamber for accommodating a strip-element stack, and having a discharging pusher with a nose for interacting with a first strip element of the strip-element stack, via a discharging slot which is adapted to the thickness of a strip element.

A dispenser of this type is known from DE-A 42 05 805. The discharging-pusher nose, which draws the first strip element of the strip-element stack into a free-standing position in which it is accessible for gripping, is configured as a tilting catch. The geometry of the latter is intended to result in a situation where the nose, when the discharging pusher is pushed inward, lifts off from the strip element and, when the discharging pusher is drawn outward, moves into a position in which the nose engages beneath the inner end surface of the strip element and carries it along. Such a discharging apparatus requires a large amount of precision well beyond the normal level. On account of prevailing tolerance pairings, ineffective displacements may occur, and these result in the user of the strip elements not being certain of the actual supply. Opening in order to make a check may result in effectiveness-reducing contact with sensitive locations of the dispensing materials.

SUMMARY OF THE INVENTION

The object of the invention is to form a dispenser of the generic type in a more functionally advantageous manner by straightforward means.

This object is achieved wherein the discharging pusher has a pusher nose which is made of elastically compliant material and, in the uninfluenced state, projects by more than the thickness of the strip element.

Such a configuration achieves a dispenser of increased use value, this is based, in particular, in the functionally reliable operation. Unproductive strokes are ruled out in practice. The carry-along part of the pusher nose acts reliably at the inner end of the strip element. It cannot slip off because the pusher nos poets by more than the thickness of the strip element. The excess pusher-nose length, which ensures transportation, simply folds over in the manner of a tongue or lip and slides over the second strip element, although the latter, as a result of not being congruent with the discharging slot, is held back. The elastically compliant, preferably rubber-like material is made to have good flexibility. It is possible to use natural rubber, synthetic rubber or even silicone. Even flexible foam material is conceivable, with or without a skin. The as it were "broom-like" gripping action of the pusher nose tolerates dimensional deviations of the strip elements, in particular, also their roughness as a result of electrically conductive crosspieces, which usually protrude slightly. All of these roughnesses, in addition that of a testing window, are easily overcome. In this respect, accordingly, it is beneficial that, in an initial dispensing position, the pusher nose projects such that it engages beneath the strip element which is ready for dispensing. It is also proposed that the pusher nose be shaped such that it projects in the form of a wedge in the direction of the strip element. This achieves a sensitive, in particular highly elastic tip which slides over the next-following strip element with a low level of contact-pressure force. As the distance from the tip increases, the nose becomes more shear-resistant. When the discharging pusher is pushed inward again, the wedge-shape causes the nose tip to return with an extremely low level of contact pressure.

In a dispenser in which, furthermore, the discharging pusher is coupled to a swing-action lid for pushing the discharging pusher inward and drawing it outward, it proves to be favorable in terms of actuation for the coupling between the discharging pusher and swing-action lid to be operationally releasable. On the one hand, this allows the favorable spatial proximity between the strip element and the discharging pusher but, on the other hand, by releasing the swing-action lid from the discharging pusher, it achieves the sought-after free-standing position which is accessible for gripping. Conversely, this automatic dispensing means can even be used for pushing the strip-element vehicle, that is to say the discharging pusher, inward. If a dispenser in which the swing-action lid forms a downwardly projecting coupling part also has the structural measure of the discharging slot being formed between the coupling part and a hinge joint of the swing-action lid, then, until the strip element is actually removed, the dispenser provides an advantageous protective space for the same. In specific terms, the details of the coupling part are such that, at its free end, the coupling part forms a latching head which engages in an elongate hole of the discharging pusher, with a longitudinal axis of the elongate hole extending in the direction of the hinge joint. In relation to the elongate hole, which forms the mating latching location, the latching head acts like a snap fastener. The elongate-hole formation takes account of the movement requirements of the coupling part. This is because there is a pivoting movement toward the head of the discharging pusher. Good adaptation to different thicknesses of a range of strip elements can be achieved in that the discharging slot is formed by interaction of an end surface of a separately latchable bar part with a housing-mounted boundary part. All that is thus required, is to insert a longer or shorter slot-dimension determining bar part. As far as the latching is concerned, it is also generally sufficient to have a sufficiently friction-fitting plug-in connection. In respect of the stack position appropriate for removal, an advantageous measure resides in the strip-element stack being loaded by a spring pusher in the direction of the strip elements dispensing position. The contact-pressure force of the spring of the spring-pusher is greater than the restoring force inherent in the material of the pusher nose. Also functionally advantageous is the measure where a viewing opening is formed in the housing of the dispenser and, if appropriate, with the swing-action lid open, allows a visual check of the spring-pusher position. As a result, the user can quickly carry out a contents check without dismantling any of the dispenser, i.e. at least without having to open the dispenser. It is also favorable here for the viewing opening to be formed in the bar part. Such verification features are thus provided on a small component rather than on the housing. Furthermore, the visual-checking means are also embodied in that a visual marker is integrally formed on the spring pusher, said marker, as the supply of strip elements decreases, being displaced into the field of view of the viewing opening. A scale or some other marking may be provided laterally on the stationary part. Furthermore, another configuration of even independent importance resides in the supply chamber being combined with the spring pusher, the discharging pusher, the discharging slot assigned to the supply chamber, and if appropriate a chamber provided with a hygroscopic material, to form a magazine which can be inserted from beneath into the housing of the dispenser, on which the swing-action lid is integrally formed. This also has the advantage of avoiding incorrect assembly insofar as some parts of the dispensing mechanism are accommodated in the supplied part, the magazine, and other parts are accommodated in the housing of the dispenser. It is also possible for the closure lid of the dispenser shaft, for example a plug-in lid, to have already been integrally formed on the magazine, which forms a so-called refill system.

If, according to a first exemplary embodiment, the strip elements which are to be separated are advanced longitudinally with sliding action over the stack-side strip element so as to be ready for removal or gripping, then the dispenser according to a second exemplary embodiment provides an advancing action such that, for dispensing purposes, a strip element is pivoted into a ready-for-removal position. This displacement, which takes place in the manner of a fanning-out action, is brought about by the pusher nose acting on the narrow edge, more precisely the bottom longitudinal side of the strip element. Accordingly the pusher nose only releases the first strip element, which is ready for dispensing, once a sub-section of the strip element has been pivoted fully out of the surface of projection of the strip-element stack. The other sub-section forms the pivot bearing. In this case, this other sub-section is gripped, as it were, on the housing side in that a wall of the housing which functions as an abutment is of friction-enhanced form on the side directed toward the strip-element stack. This can easily be achieved in that that side of the wall which is directed toward the strip-element stack is rubber-coated. For easy-grip access to the discharging pusher and/or the pusher nose, it proves to be favorable for the wall only to extend over part of the length of the strip-element stack. Moreover, said wall is set back slightly in relation to the exposed rubber-coating. The strip element is exposed in its sub-section which interacts with the discharging pusher, a penetration space being formed in the process. Here too, the strip element is advanced into the manual gripping position by using functional parts of the dispenser provided. Use is made of the swing-action lid. Accordingly, as a development, it proves to be advantageous for the discharging pusher to be part of the swing-action dispenser lid, of which the hinge-joint axis of rotation runs parallel to the displacement direction of the spring pusher. It is advantageous here for the spring pusher to be subjected to the action of a spring which acts with variable spring force. The spring forms a transporting finger which moves back and forth. The corresponding action is directed so as to ensure that the strip-element stack is pushed up forcibly into position, and also such that the clamping action on the gripped sub-section is sufficient, but removal can take place smoothly. Accordingly, the spring force is reduced when the strip element is pivoted out; the "brake" is released slightly. A further advantageous feature of the invention resides in the spring force being varied by the swing-action lid, which acts on a precurved spring spine, in dependence on the position of the swing-action lid. The pressure on the spring spine decreases during opening. In this context, it is also proposed that the free end of the spring interacts in the manner of a ratchet with a toothed bar of the spring pusher. It is then advantageous for a push rod which acts on the spring spine to be formed on the inside of the swing-action lid. The push rod pushes in the spring spine, which is precurved outward, i.e. in the direction toward the push rod, with the result that the spring pusher is advanced. It is then proposed for the strip-element stack and the spring to be covered over by a cover plate, the cover plate having an opening assigned to the spring spine. This provides the accessibility which is required for the push rod to act on the spring spine. As far as the monitoring of the filling level of the dispenser is concerned, it is also advantageous in the present exemplary embodiment for the cover plate to have a viewing opening which releases part of the strip-element stack. Here too, the cover plate can be used to form different discharging slot extents. In respect of the dispenser mechanism, another advantageous solution, then, resides in the axis of rotation of the hinge joint of the swing-action lid and a pivot axis of the strip section which is to be dispensed running parallel to one another, but at a distance apart, it being the case that, with the swing-action lid closed, the pivot axis of the strip element is offset in the direction of the discharging pusher, and at a lower level, relative to the axis of rotation of the hinge joint of the swing-action lid. This results in different arcuate paths. These run radially such that the pusher nose which draws upward into the ready-for-removal position the strip element which is to be dispensed and loses contact, in this position, with the lower edge of the strip element. From this position, the swing-action lid, released from its carry-along function, can be swung open freely to the full extent.

BRIEF DESCRIPTION OF THE DRAWINGS

The subject matter of the invention is explained in more detail hereinbelow, with reference to two exemplary embodiments illustrated in the figures, in which:

FIG. 1 shows, true to scale, a side view of the dispenser according to a first exemplary embodiment, FIG. 2 shows the plan view for FIG. 1, FIG. 3 shows a view in the direction of a narrow side of the dispenser.

FIG. 9 shows the dispenser with the strip element advanced into a free-standing position in which it is accessible for gripping and with the swing-action lid swung away to a sufficient extent, that is to say uncoupled, FIG. 10 shows the section along line X—X in FIG. 5, FIG. 11 shows a vertical section taken along line X—X with the swing-action lid located in position according to FIG. 9, FIG. 12 shows, true to scale, a side view of the dispenser according to a second exemplary embodiment, FIG. 13 shows, a view in the direction of a narrow side of the dispenser, FIG. 14 shows the plan view of FIGS. 12 and 13, FIG. 18 shows the housing of the dispenser with the spring-action lid open, FIG. 19 shows the cover plate on its own, FIG. 20 shows the spring pusher, FIG. 21 shows a strip-element stack, FIG. 22 shows the spring, FIG. 23 shows two drying-medium blocks.

FIG. 30 shows, likewise in schematic representation, an intermediate position in this respect, and FIG. 31 shows a perspective view of the dispenser with the swing-action lid swung into a vertical position, leaving behind a large gripping region for gripping and drawing the strip element which has been pivoted into the ready-for-removal position.

DETAILED DESCRIPTION OF THE PREFERRED EMBODIMENT

Figure 4:
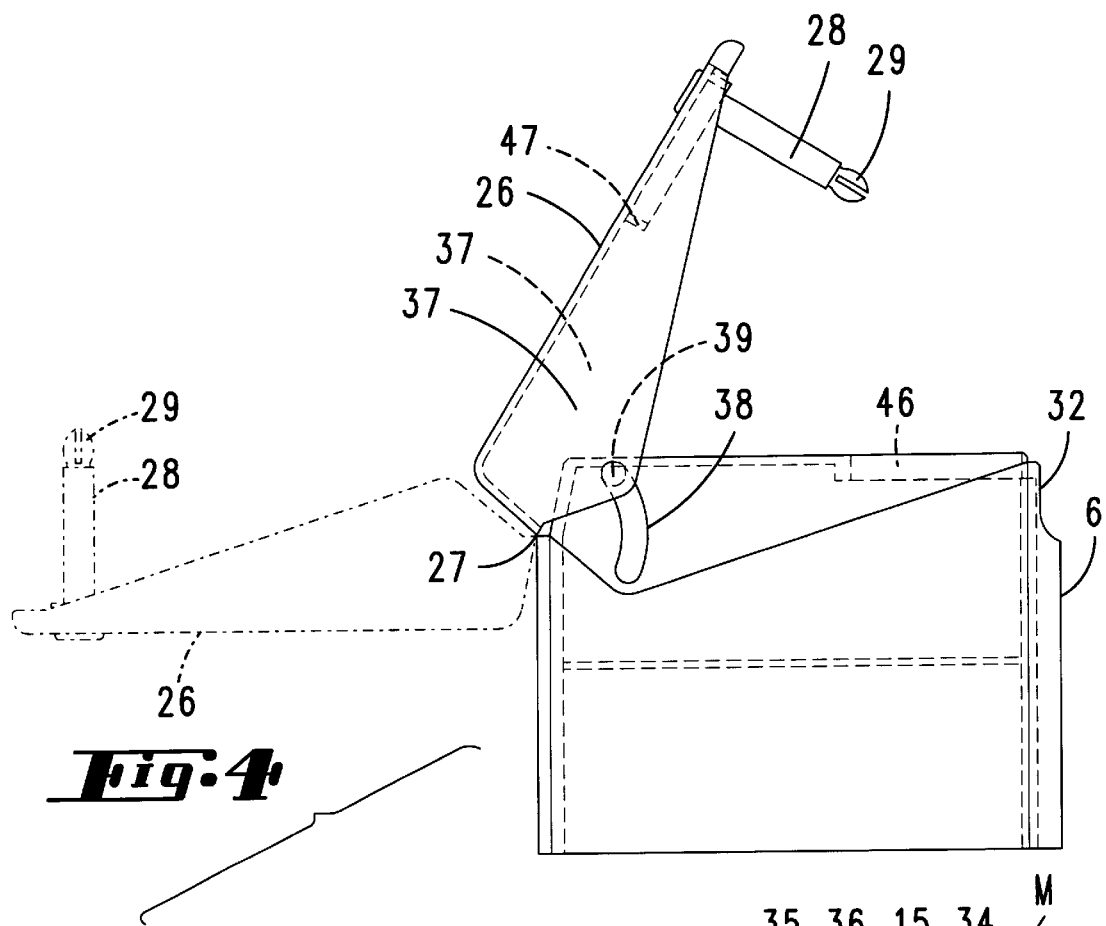
FIG. 4 shows an exploded illustration of the dispenser together with the dispensing material.

The dispenser 1 illustrated contains a dispensing mechanism 2 by means of which its dispensing material accommodated in a supply chamber 3, in this case, strip elements 4, are presented such that they are accessible for gripping. These strip elements are, for example, test strips for testing the sugar level in blood or urine.

The supply chamber 3 is intended for accommodating a strip-element stack St. The strip elements 4 extend vertically in the upright position of the flat-body dispenser 1 which can be seen from FIG. 1. A correspondingly aligned wall 5 of the housing 6 of the dispenser 1 orders the strip elements in this respect.

The first strip element 4' directed toward the dispensing mechanism 2, is positioned against the inner surface 5' of the wall 5 of the housing 6, said inner surface being directed toward the supply chamber 3.

Figure 5:
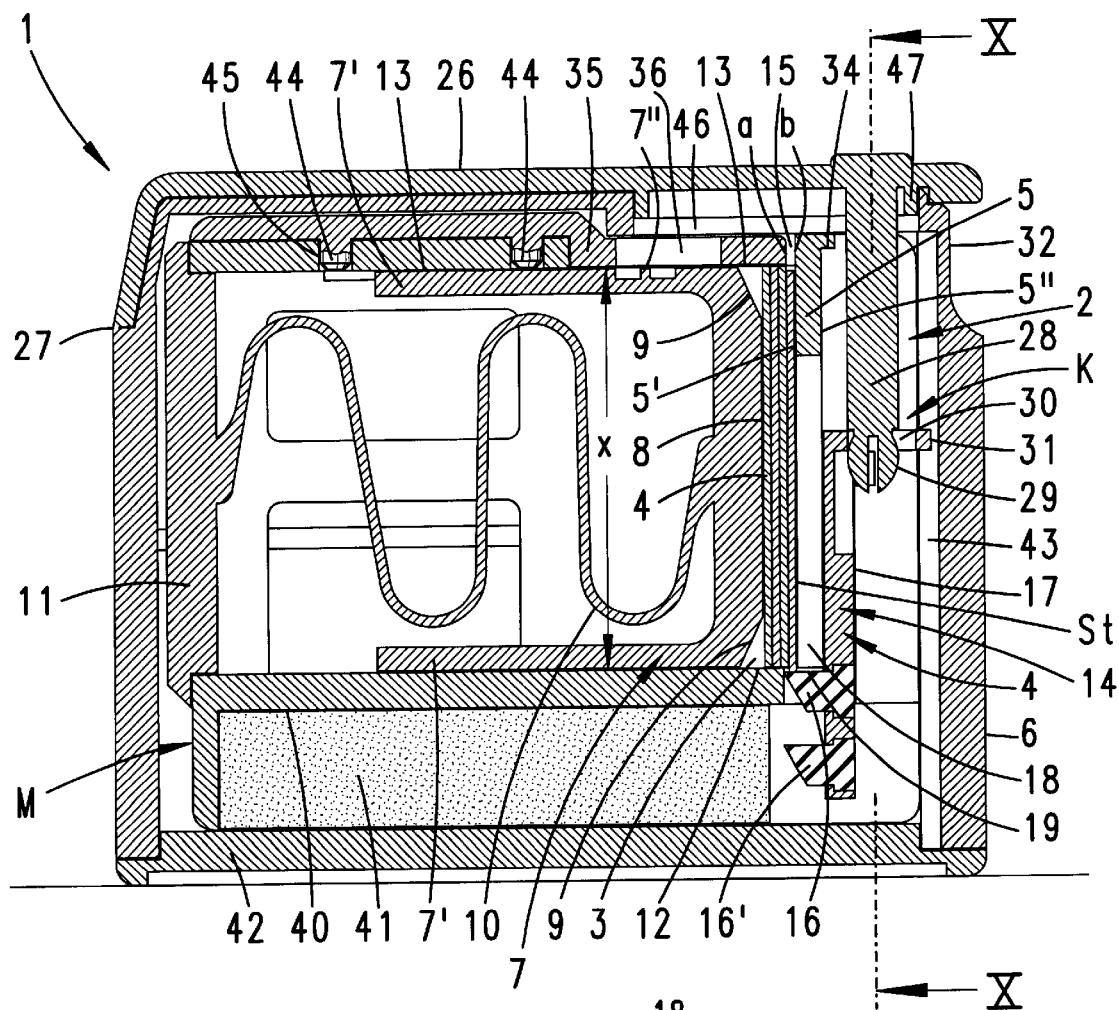
FIG. 5 shows, on a larger scale than FIG. 2, the section along line V—V in FIG. 2, to be precise in the basic position of the dispenser.

The last strip element of the stack St is subjected to the action of a spring to give the ordered bundle formation, as can be seen, for example, in FIG. 5. Use is made of a spring pusher 7. The end or outer surface 8 of the latter runs parallel to said inner surface 5' of the wall 5. The outer surface 8 merges into a bevel 9 in each case in the direction of the top and bottom end regions. A spring 10 is integrally formed on the rear of the spring pusher 7. Said spring is an integral constituent part of the spring pusher 7 and is prestressed. The spring pusher 7 is a U-shaped body. It opens in the direction of a closure plate 11, by means of which the rear region of the supply chamber 3, it being possible for said rear region to be used as a spring chamber, is kept closed. The closure plate 11 is arranged with a friction fit, but may also be latched.

The supply chamber 3 or spring chamber has a height x, which is somewhat greater than the length of the strip elements 4. An arrangement which is sought after and achieved here is one which has sufficient sliding play for the strip-element stack St to be pushed up in the direction of the dispensing mechanism 2 without any disruption. The bottom termination of the supply chamber 3 is formed by the base 12 of the latter; the top termination here is formed by the cover 13. The base 12 and cover 13 also serve as guide surfaces for the U-legs 7' of the spring pusher 7.

The operation of discharging the respectively first strip element 4' of a strip element stack St into a free-standing position, in which it is accessible for gripping, above the cover 13, takes place with the aid of a discharging pusher 14. This takes place via a discharging slot 15 of the housing 6. The slot is located in the cover 13.

Figure 6:
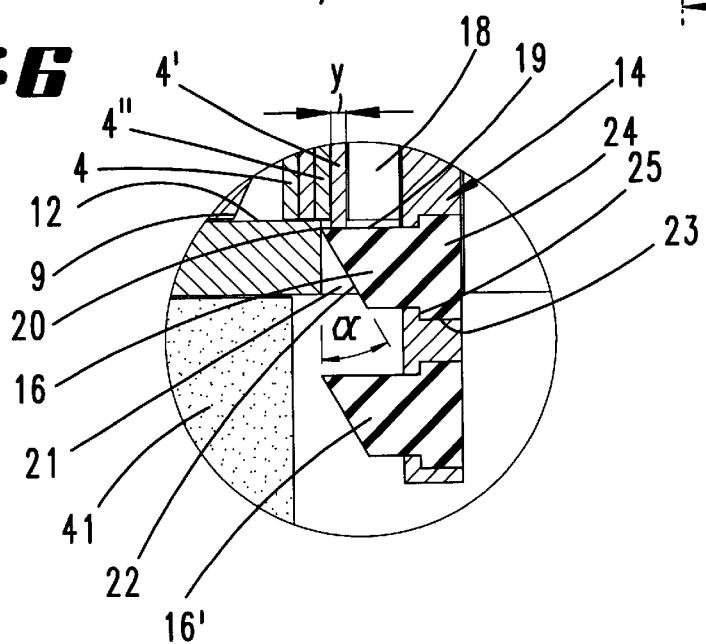
FIG. 6 shows an enlargement from FIG. 5.

The discharging slot 15 runs congruently with the first strip element 4' supported in its ready-for-dispensing position. This alignment can be gathered clearly, for example, from FIG. 5, from which it is also possible to see that the discharging slot 15 is adapted to the thickness of a strip element. The thickness is designated y and this designation is indicated in the enlargement of FIG. 6.

The actual carry-along element of the discharging pusher 14 is a pusher nose 16. This projects horizontally from the discharging pusher 14. The latter is set back from the nose 16 to a sufficient extent for guidance purposes. It slides in lateral guide grooves 17 in the interior of the housing 6. The guide grooves 17 are directed outward in the rear of the wall 5. They run parallel and accommodate the narrow sides of the discharging pusher 14. The rear is taken as the outer surface 5".

In order to reach into the region of the strip element stack St, the wall 5, open from beneath, is provided with a through-passage slot 18. The clear width of the latter corresponds at least to the diameter of the pusher nose 16, which is basically in the form of a cylindrical stub. The diameter of said pusher nose takes up approximately half the width of the discharging pusher 14. It is seated centrally.

As can be gathered from the drawing, the pusher nose 16 projects by more than the thickness y of a strip element 4. The horizontal flank 19 of the pusher nose 16 thus engages reliably beneath the bottom end surface of the strip element 4'.

In the basic position, the tip 20 of the pusher nose 16 also passes into the region of the second strip element 4" on the dispensing side (see FIG. 6). The slot insert 21 is cut back correspondingly there at the base, with the result that at least a third of the end surface of the second strip element 4" is still supported at the base. The second strip element projects with its relevant end right up against the cover 13, as do all the following strip elements; this is in contrast to the situation below, where the pusher nose 14 projects by considerably more than the thickness y of the strip element 4', which is ready for dispensing. It is even possible here for the pusher nose to engage beneath three or four strip elements 4 (not illustrated). All that would be necessary for this purpose would be for the base 12 to be cut back further to some extent, to be precise in accordance with the diameter of the pusher nose 16. The remaining lateral surface of the base 12 functions as a support for the strip elements 4. This produces a horizontally deeper slot inlet 21.

Typical of the nose form, the pusher nose 16 is shaped such that it projects in the form of a wedge in the direction of the strip element 4'. The wedge shape is formed by the oblique flank 22 which forms the rear of the nose. The bevel angle alpha may be a good 30°.

The undercut-like course of the flank 22 aids a yielding return of the pusher nose 16, that is to say when the discharging pusher 14 is drawn inward. The friction-fitting functioning is then minimized, this also being aided by the material selection described.

The pusher nose 16 is located in a mount 23 of the discharging pusher 14, which is made of relatively rigid material.

The mount 23 is cup-shaped. Its diameter is larger than that of the cylinder-stub-like pusher nose 16. The diameter of the base 24 of the pusher nose 16 is adapted in order to fill the mount. A shoulder 25 which results from the difference in the diameters of the mount 23 and of the pusher nose 16 forms a plug-in limiting stop, with the result that it is ensured that the tip 20 has a sufficient grip-over projection.

Located at a short vertical distance beneath the pusher nose 16 in the basic position in the slot inlet 21, on the discharging pusher 14, is a second, identically formed and arranged pusher nose 16'. This gives functional reliability over an extremely long period of use, for example in the case of the tip 20 of the top pusher nose 16 being worn away. The noses 16, 16' are formed, and also arranged, identically.

The discharging pusher 14 is actuated from the outside. For this purpose, use may be made of a type of push button. Preferred and illustrated, however, is a dispensing operation which takes place in dependence of the actuation of a pulling element. For this purpose, the dispenser 1 has, above the cover 13, a swing-action lid 26. The latter pivots about a hinge joint 27. The latter is located on that narrow side of the housing 6 which is directed away from the dispensing mechanism 2.

That end of the cap-like swing-action lid 26 which is remote from the hinge joint bears a coupling part 28 which is oriented downward i.e. in the direction of the discharging pusher 14. Said coupling part has already been integrally formed on the swing-action lid 26, in the same way as the swing-action lid 26 is an integral constituent part of the housing 6, with the result that the hinge joint 27 is formed as a film hinge. The demolding position can be gathered from FIG. 4. It is represented, as far as the swing-action lid 26 is concerned, by chain-dotted lines.

The swing-action lid 26, which serves for pushing the discharging pusher 14 inward and drawing it outward, is located in a releasable coupling K between the discharging pusher 14 and swing-action lid 26.

Use is made of a snap-fastener-like coupling K. A latching head 29 integrally formed at the free end of the coupling part 28 functions as the male part. Said latching head has cross slots. The female connecting element is an extension arm with an elongate hole 30. The latter is located in a horizontally running leg 31 of the discharging pusher 14, said leg projecting away from the supply space. This produces an L-shaped angle profile.

Figure 7:
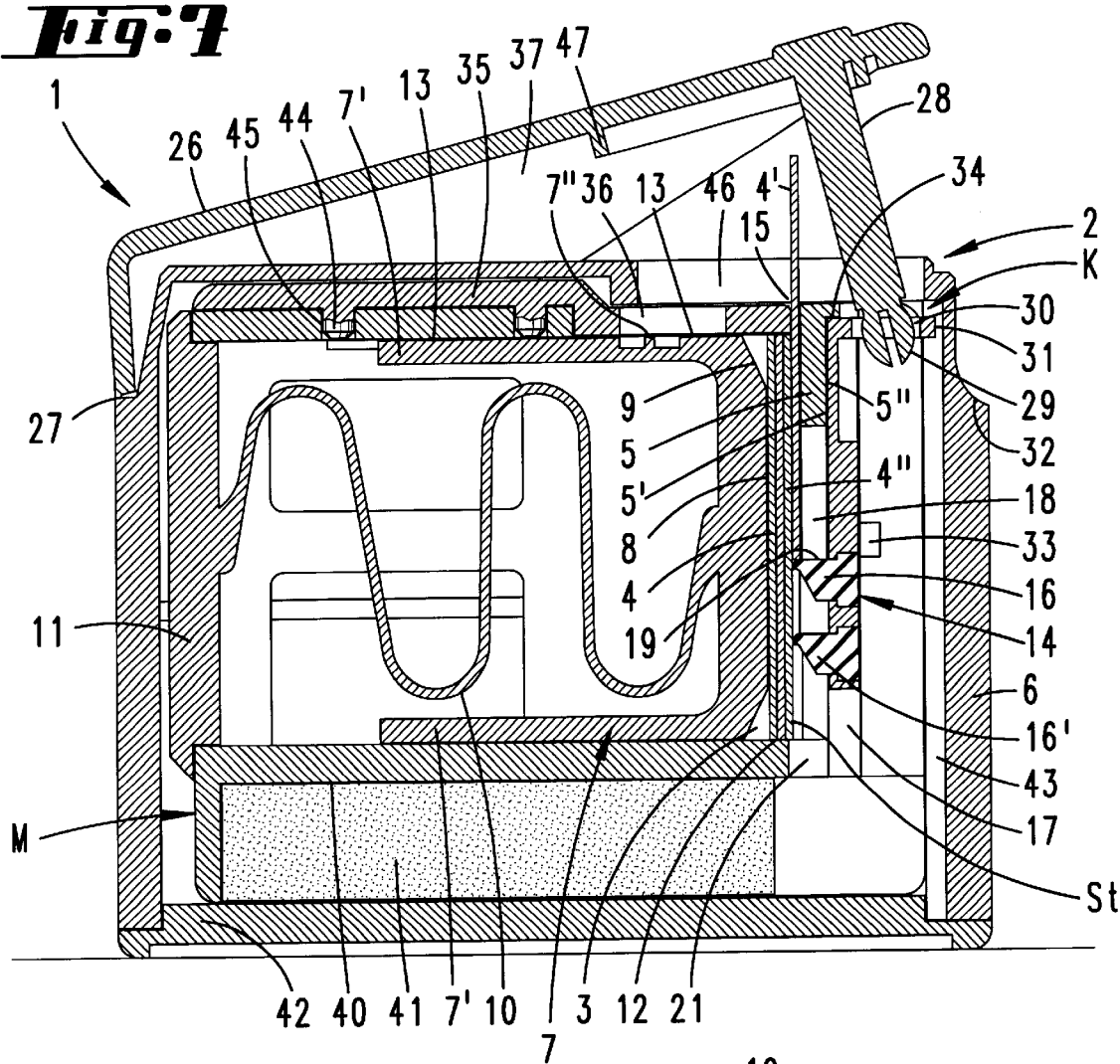
FIG. 7 shows the dispenser in an illustration like that of FIG. 5, but in an intermediate actuating position, i.e. with the swing-action lid not yet uncoupled.
Figure 8:
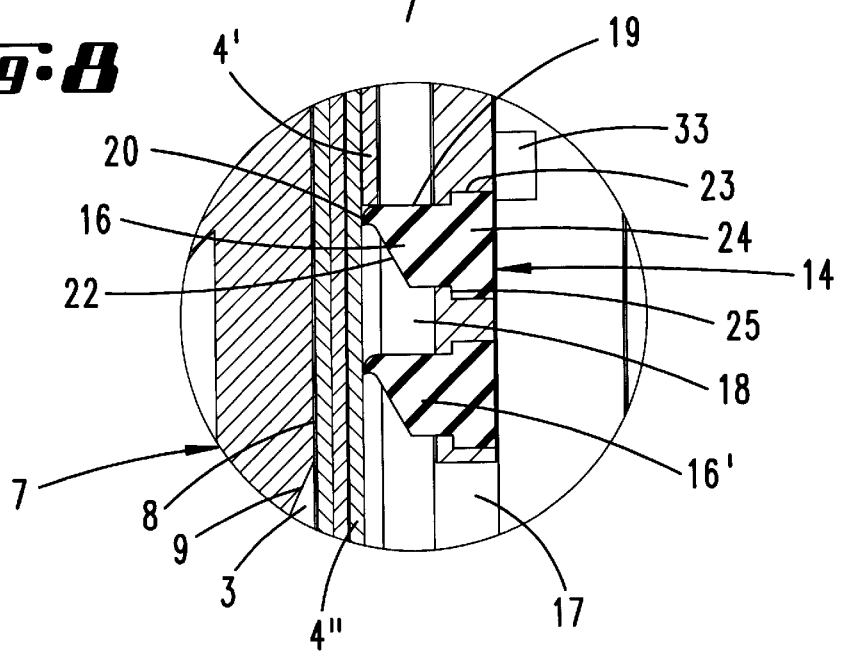
FIG. 8 shows an enlargement from FIG. 7.
Figure 15:
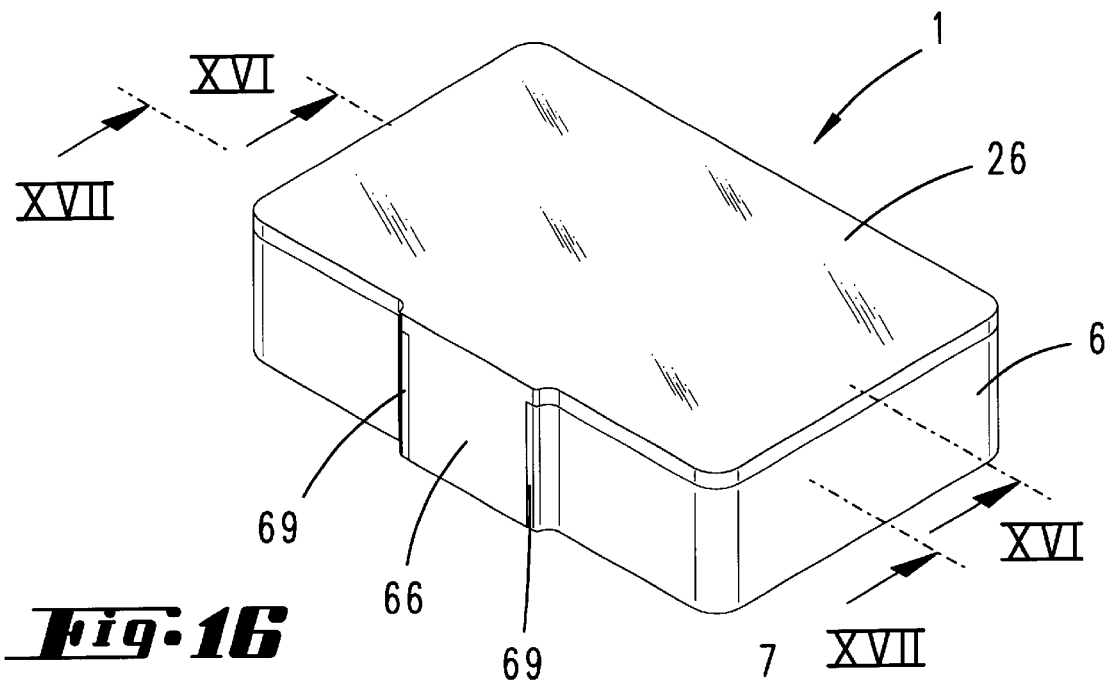
FIG. 15 shows a perspective illustration of a slightly enlarged dispenser with the swing-action lid closed.
Figure 16:
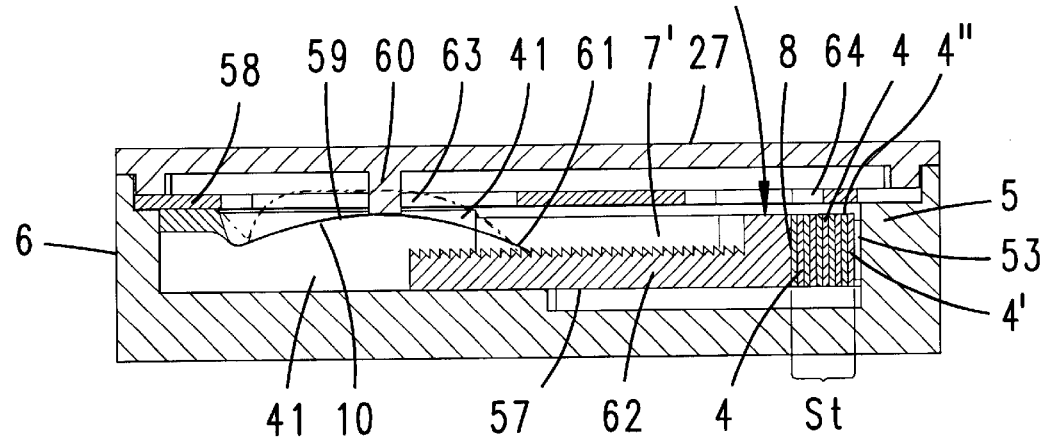
FIG. 16 shows the section along line XVI—XVI in FIG. 15, in a plane through the toothed bar of the spring pusher and with the spring exerting an advancement force in the dispenser.
Figure 17:
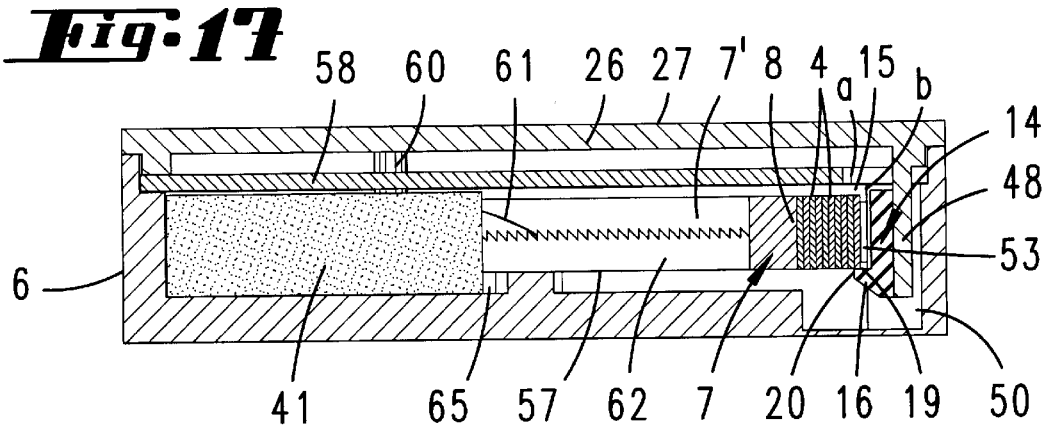
FIG. 17 shows the section along line XVII—XVII in FIG. 15, in a plane through the discharging pusher and the pusher nose thereof.
Figure 25:
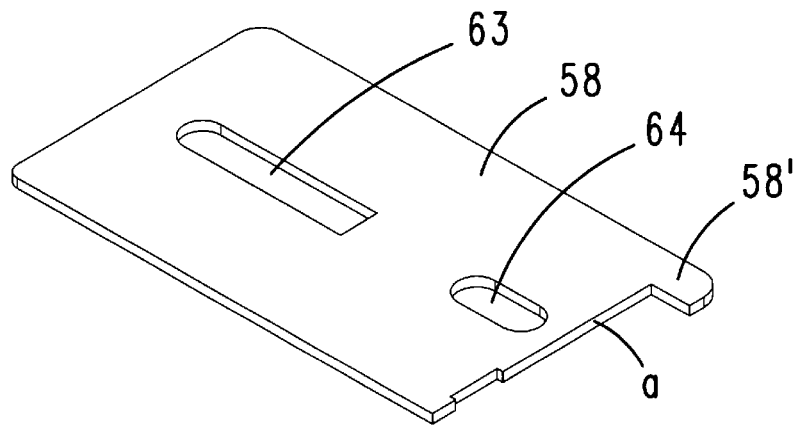
FIG. 25 shows the cover plate in correctly assigned alignment as a closing part which can be latched to the housing.
Figure 24:
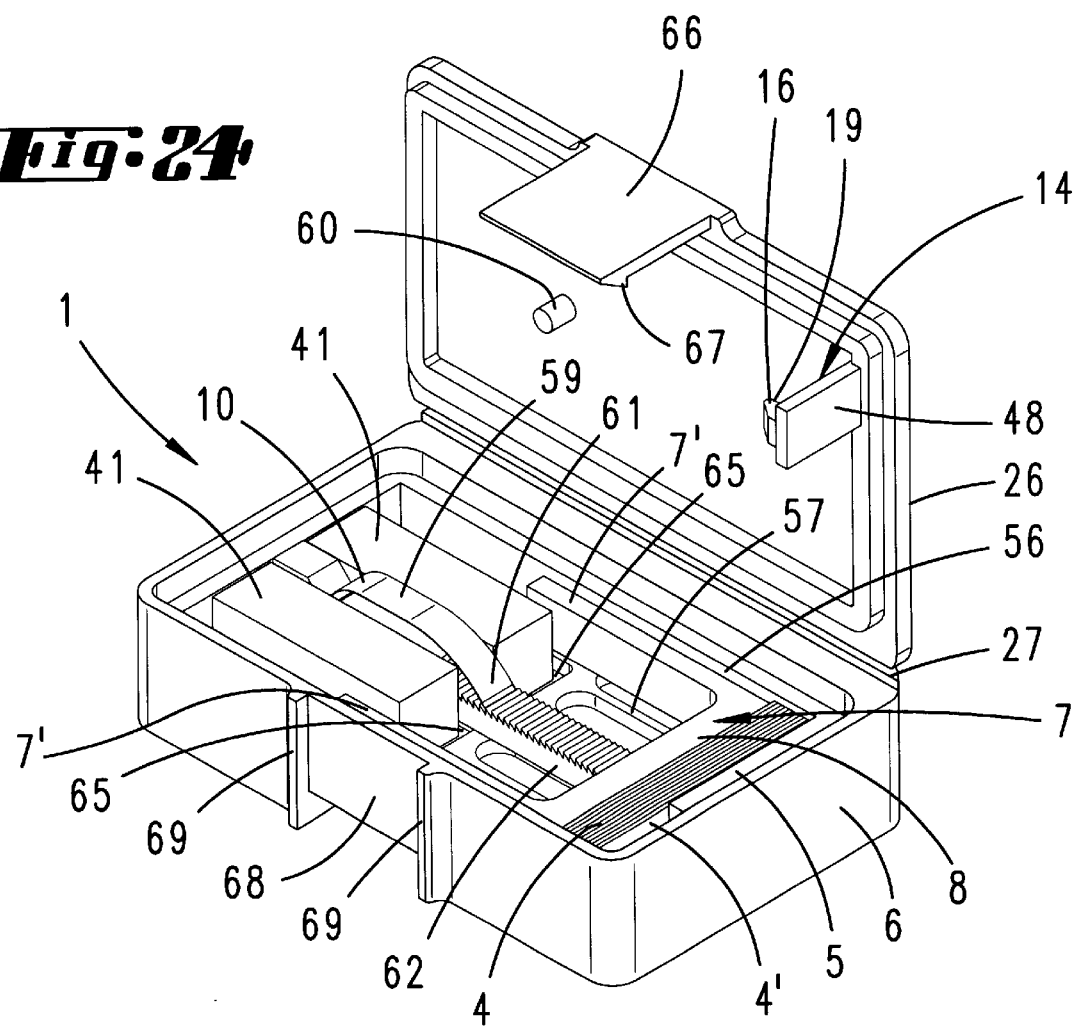
FIG. 24 shows a perspective view of the housing of the dispenser, in this case accommodating the parts according to FIGS. 20 to 23.
Figure 26:
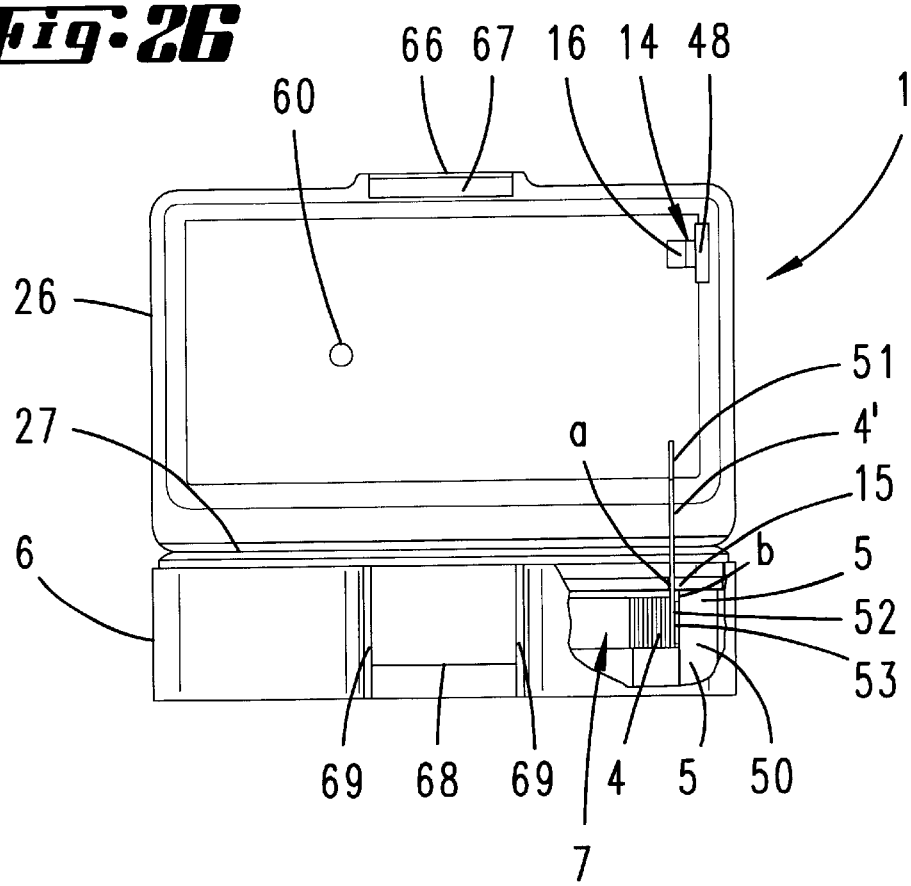
FIG. 26 shows, in partially broken-away form, a side view of the dispenser with the swing-action lid open.

As far as the pivoting movement of the swing-action lid 26 is concerned, the elongate hole 30 provides the space for the coupling part, which passes into the female part in a somewhat tilted manner. This situation can easily be seen from FIG. 7. Accordingly, the axis of the elongate hole 30 is located in the plane of the pivoting movement, that is to say it is oriented in the direction of the hinge joint 27.

Heightwise, the hinge joint 27 is located approximately halfway up the peg-like coupling part 28; this is based on an imaginary horizontal line intersecting the geometrical axis of the hinge joint 27.

For easy gripping of the free end of the swing-action lid 26, the housing 6 of the dispenser 1 is hollowed out beneath said end. The hollow, which is of approximately fingertip-sized dimensions, is designated 32.

In the basic position (FIG. 5), the latching head 29 has passed into the elongate hole. In this basic position, the discharging pusher 14 assumes a stop-limited end position. Stop protuberances for this purpose are located in the vicinity of the guide grooves 17 and are designated 33 (you are referred to FIG. 10). There, the angled legs 31 come into contact with the top side of the stop protuberances 33. Said stop protuberances 33 are shaped, and can be overcome, such that, for assembly purposes, the discharging pusher 14 can be fitted from beneath.

A top limiting stop is formed by a horizontal lower edge 34 of the wall 5 of the housing 6. The lower edge 34 projects on the coupling-part side, but terminates at a sufficient distance from said coupling part 28.

It is possible for the discharging slot 15 to vary in adaptation to different thicknesses of strip elements 4. For this purpose, part of the cover 13 of the housing 6 can be removed. In specific terms, this takes place such that the discharging slot 15 is formed by interaction of a vertical end surface a of a separately latchable bar part 35 with a housing-mounted boundary part, in this case of the wall 5. Said boundary part is formed by the vertical end surface of the discharging slot 15 which is designated b. The last-mentioned end surface b continues flush, as a sliding surface, into the stack-supporting inner surface 5' of the wall 5. As has already been indicated, the strip-element stack St is loaded by the spring pusher 7 in the direction of the strip-element dispensing location.

The variation by virtue of a greater or smaller projecting length of the end surface a of a replacement part is more favorable than changing the basic version of the dispenser in the region of the mechanism.

The bar part 35 is also given a further function. This resides in the bar part 35 having a viewing opening 36. Of course, it could also be possible for the latter to be realized in a section of the housing 6 of the dispenser 1. In the case of the subject matter illustrated, the viewing opening 36 is covered over by the swing-action lid 26. Swinging the latter open allows a visual check to be made; for example, the spring-pusher position may serve as a filling-level indicator. A visual marker 7" is integrally formed on the outside of the spring pusher 7 to be precise on the top leg 7' of the same. As the supply strip elements decrease, the visual marker 7" moves into the field of view of the stationary viewing opening 36, of which the longitudinal-border edge has a filling-level scale, with the result that the user can easily detect the filling level of the dispenser. The viewing opening 36 is located in the vicinity of the slot, in which the largest gripping and/or viewing clearance is provided in the swung-open position. The discharging slot 15 extends between the coupling part 28 and the hinge joint 27 of the swing-action lid 26 such that initially (see intermediate phase of FIG. 7) the strip element 4' raised into the free-standing position, in which it is accessible for gripping, is protected by the peg-like coupling part 28 and also by side walls 37 of the swing-action lid 26, said side walls tapering in the direction of the free end of the swing-action lid 26.

As can be seen from FIG. 4, the side walls 37 are also used for forming a swing-open limiting position of the swing-action lid 26, comprising an arcuate groove 38 on the housing 6, which extends about the geometrical axis of the hinge joint 27 and in which an end-stop-providing stub 39 runs. The latter is realized on the inside of the two side walls 37. A tight closure is ensured in respect of the lid 26, for example, by an angled joint being realized between the swing-action lid 26 and the head of the dispenser 1.

A chamber 40 is located beneath the supply chamber 3. The chamber 40 accommodates a drying medium block 41. Such a hygroscopic material may be formed by zeolite, silica gel or the like. The chamber 40 is in open connection with the shaft-like dispensing section of the dispensing mechanism 2. The housing 6 terminates with a plug-in cover 42 beneath the chamber 40. Said cover is secured by latching and can be drawn off at will.

The dispenser 1 can be loaded from the rear, via a closure wall, or as is preferred, using a magazine M. In the latter case, the procedure is such that the supply chamber 3 is combined with the spring pusher 7, the discharging pusher 14, the discharging slot 15 assigned to the supply chamber 3, and as appropriate, a chamber 40 provided with the hygroscopic material, to form the magazine M. The latter is inserted from beneath into the housing 6 of the dispenser 1, on which the swing-action lid 26 is integrally formed. It is also possible for the plug-in lid 42 to be fixed to the magazine M.

The magazine M can only be arranged in the correct position since the leg 21 projects beyond the dispensing-mechanism narrow side and only there can project into a vertical longitudinal slot 43 on the inside of the housing 6. Since the other narrow side of the dispenser 1 has no such equivalent on the inside, the dispenser 1 can only be assembled correctly.

As far as the bar part 35 is concerned, it should also be pointed out that this can be retained simply via pegs 44 which engage in a friction-fitting manner and project into congruent holes 45 of the housing 6 or of the magazine M.

In respect of the means for checking contents, it should also be mentioned that the viewing opening 36 can also be seen from the housing through a hatch 46 of the housing cover. Said hatch 46 is dimensioned here such that it also forms the through-passage window for the first strip element 4' lifted out. The hatch 46 here is an elongate hole which terminates just before the inlet of the vertical longitudinal slot 43. The sealing closure of the hatch takes place via a closing collar 47. The latter has already been integrally formed on the underside of the swing-action lid 26.

Functioning is, briefly, as follows: starting from the position according to FIG. 5, the swing-action lid 26, which functions as an actuating handle, is swung open. As a result of the coupling K, the pivoting movement results in the discharging pusher 14, which is guided in the manner of a carriage, being carried along. The pusher nose 16 of said discharging pusher carries along the first strip element 4', beneath which it engages. The, pusher nose engages beneath the strip element in a manner in which it is secured against slipping since the full end cross section thereof and of further elements is gripped. In respect of the further elements, however, the projecting tip 20 folds over downward and thus, as it were, "grazes" over the second strip element 4" of the stack St, although said second strip element is held back on the cover 13. This is the situation according to FIG. 7, in which the top end of the discharging pusher 14 has come into contact against the stop-forming lower edge 34.

Pivoting the swing-action lid 26 further at will eliminates the coupling K between the drawing and drawn elements. This gives the stop-limited, that is to say maximum, swung-open position according to FIG. 9. The free-standing position which is accessible for gripping has been reached. It is maintained in a friction-fitting manner. Following removal, the dispenser 1 can be closed again by the swing-action lid 26 being pivoted back into its starting position. In this case, the coupling part 28 functions as a push rod. The latching head 29 of the latter comes into contact with the border of the elongate hole 30. This results in the discharging pusher 14 being pushed inward. In this case, the tip 20 folds over in a sloping manner. It slides over the next strip element until the pusher nose 16 has passed into its basic position, i.e. into the ready-for-carrying-along position, which can be seen in FIG. 5 and in which the flank 19 grips beneath the end over a certain thickness. This situation can clearly be seen from FIG. 6. For reasons of clarity, the flank 19 is illustrated as being slightly lower than the base 12.

As far as the advancement of the first strip element 4' being brought about by the swing-action lid, the dispenser according to a second exemplary embodiment (FIGS. 12 to 31) is of basically the same construction. The designations are used analogously, in some cases without being repeated in the text. If the strip-element stack St according to the basic version, i.e. the first exemplary embodiment, is separated in the longitudinal direction of the strip elements 4, then, according to the second exemplary embodiment, the first strip element 4' in the dispensing direction is pivoted into a ready-for-removal position for dispensing from the dispenser 1. It assumes an oblique removal position which is located approximately at 45° to the planar extent of the housing 6, which in this case is formed as a flat box.

The inherent lengthwise extent of corresponding test strips, i.e. strip elements 4 is used by one sub-section being retained with a gentle clamping action in the plane of the stack St until removal and another sub-section, that is to say the other end of the strip element 4, functioning as a gripping surface. The thumb and forefinger can easily be placed in position there. In addition, the location is clearly visible.

For the corresponding pivoting of the discharging pusher 14 running over an arcuate path, even just a relatively small pivoting displacement is sufficient.

The discharging pusher 14 is part of the swing-action dispenser lid 26. It is integrally formed thereon and is seated on a freely projecting carrier 48. Here too, the pusher nose 16 is made of elastically compliant material. In the closed position of the dispenser 1, the pusher nose, ready for lifting out, is located beneath the bottom longitudinal side 49 of the strip element 4, which has a long rectangular cross section. The horizontal flank 19 engages beneath. It is also possible here for the tip 20 to project beyond the thickness y of the strip element, with the effects explained above.

The supply chamber 3, which accommodates the strip-element stack St, is wall-bounded. The wall is designated 5 and has already been molded along with the housing 6. The strip-element-stack assembly, which is subjected to spring loading, is supported on the wall 5.

It can be seen that the wall 5 only extends over part of the length of the strip-element stack St. The part which is set back in relation to the wall 5 leaves behind a sufficient penetration space 50 for the pusher-containing carrier 48 together with the discharging pusher 14.

The sub-section 51, beneath which the pusher nose 16 engages, can thus easily be reached by the, lifting-out pusher nose 16.

The other sub-section 52 is rotationally secured, it is supported on the wall 5 and is subjected to stack-securing loading by the spring pusher 7. Moderate clamping is achieved, which is also varied. In respect of the wall 5, there is even a friction-enhancing action in the direction of the first strip element 4', which is ready for dispensing. This wall 5 is rubber-coated on the side directed toward the stack. The corresponding rubber layer, illustrated as being exaggeratedly thick, is designated 53. It is depicted such that it is visible from the front as a rectangular zone in FIG. 27. This friction-enhancing measure avoids the situation where a, for example, relatively heavy strip element 4 drops back into the supply chamber 3, following release by the lifting-out pusher nose 16.

The first strip element 4' is pivoted about the region of the sub-section 52. A pivot axis 54 is produced in practice here. Said pivot axis is defined by a pocket formation 55 in the housing. The pocket is also formed by a vertical rear wall 56, a carrying rib of a base grid 57 in the vicinity of the rear wall, and a top horizontal section 58' of a cover plate 58 of the housing 6, said cover plate being inserted in the vicinity of the swing-action lid.

The swing-action lid 26 and the strip element 4' thus pivot about different centers. The swing-action lid 26 pivots about the horizontal hinge axis 27 over an arcuate path B1. The radius in this respect is designated r'. In contrast, the strip element 4' which can be moved out obliquely rotates in a vertical plane about the pivot axis 54. The radius thereof is designated r" and the associated arcuate path is designated B2. The axis of rotation of the hinge joint 27 of the swing-action lid 26 and the pivot axis 54 of the strip element 4' are located parallel to each other in space. Their spacing apart from one another can clearly be seen from FIG. 27. It can be seen that, with the swing-action lid 26 closed, the pivot axis 54 of the strip element 4' is offset horizontally and downward in the direction of the discharging pusher 14 relative to the axis of rotation of the hinge joint 27 of the swing-action lid 26.

Figure 27:
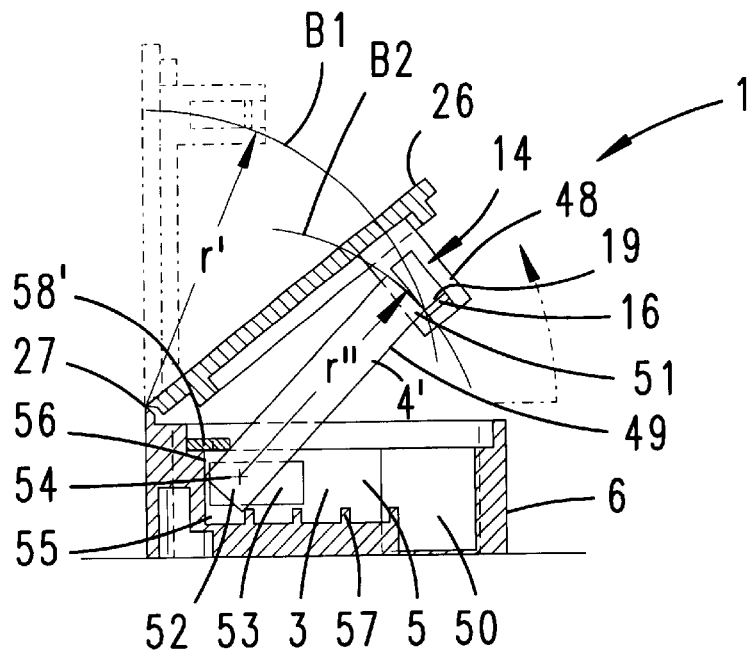
FIG. 27 shows a cross section through the dispenser just before disengagement of the discharging pusher running over an arcuate path.
Figure 28:
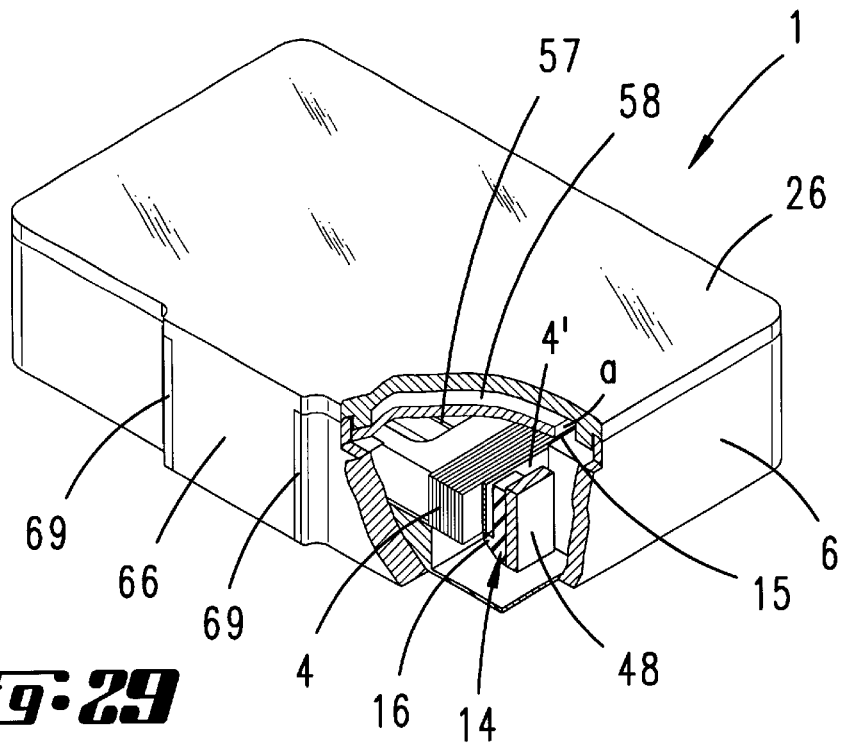
FIG. 28 shows a perspective view of the dispenser with the corner region broken away.
Figure 29:
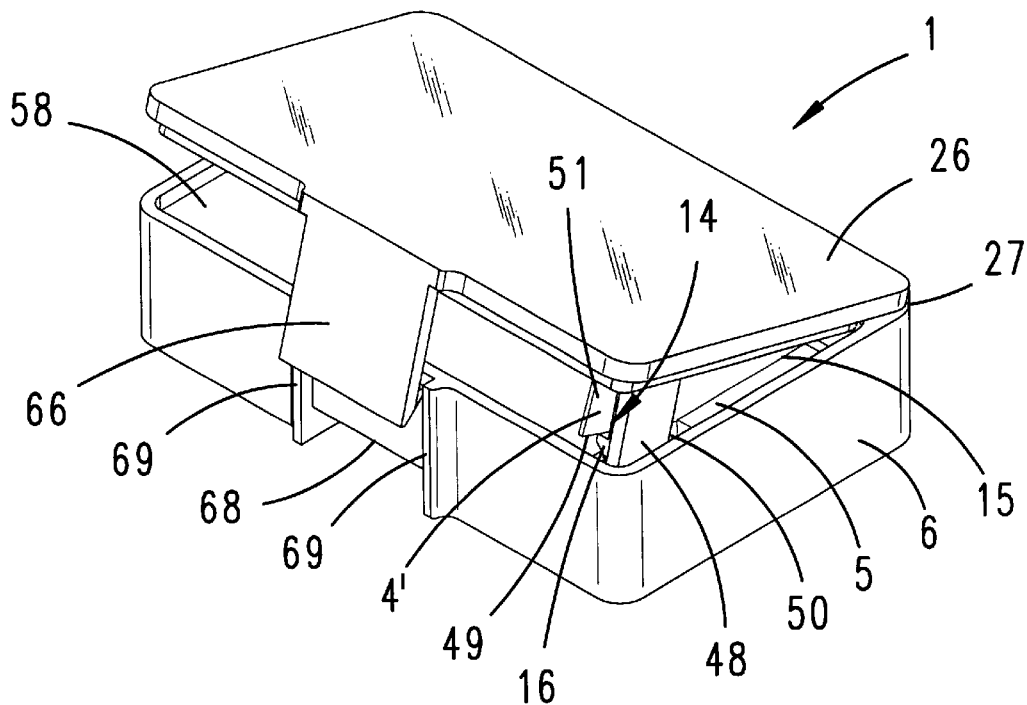
FIG. 29 shows an illustration corresponding to FIG. 28 at the start of the pivoting-out operation of the first strip element.

In the position which can be seen from FIG. 27, the divergence of the circular arcuate paths B1 and B2 results in the lifting-out action being eliminated; the free end of the bottom longitudinal side 49 of the strip element 4' slides, as it were, off from the flank 19 of the discharging pusher 14, but remains in place as a result of the friction enhancement described, in other words the first strip element 4' which is ready for dispensing, has its sub-section 51, which interacts with the discharging pusher 14, exposed. In this case, the sub-section 51 of the strip element 4' has been pivoted fully out of the surface of projection of the strip-element stack St.

Here too, the stack-retaining spring is designated 10. It is configured separately. It extends essentially in the form of a leaf-spring body in the longitudinal direction of the dispenser 1, that is to say in the displacement direction (arrow z in FIG. 31) of the spring pusher 7 advanced by it.

The spring 10 is arcuate in the longitudinal direction. The vertex of the arcuate curve is directed toward the underside of the swing-action lid 26. The inside of the swing-action lid 26 acts on the spring spine 59 which is curved in this way. This takes place via push rod 60. The latter is integrally formed such that it projects from the inside of the swing-action lid 26 congruently with the spring spine 59.

The peg length is coordinated with the end phase of the closing movement of the swing-action lid such that the spring spine 59 is pushed down, and this can take place until more or less a straightened-out position has been reached. The lengthening transferred from the arcuate shape into the chord is used for the advancement of the spring pusher 7. That end of the spring 10 which is directed away from the supply chamber 3 is stationary. That end of the spring 10 which is directed toward the supply chamber 3 forms a ratchet tongue 61. This interacts with tooth gaps of a toothed bar 62 of the spring pusher 7.

The latching tongue 61, which is inclined downward, i.e. in the direction of the base grid 57, interacts, for the advancement, with the steep flank and, for the free return, with the obliquely positioned rear flank of the teeth of the toothed bar 62. Excess displacement is compensated for in each case by the flexibility of the body of the spring 10. With the return, slight pressure relief takes place in relation to the strip-element stack St. Such pressure relief is present with the swing-action lid 26 open. This, as a result of a certain reduction in friction, accounts for the easy operation of drawing the strip element 4' out of its secured position. The certain amount of loosening also prevents the next-adjacent strip element 4" from being drawn out as well. The spring pusher 7 itself is retained in its guide of the housing 6 in a friction-fitting manner. It can thus be seen that the spring pusher 7 is subjected to the action of a spring 10 with variable spring force, with the advantageous effect that the spring force is reduced when the strip element 4' is pivoted out. Initially, i.e. approximately in the open position according to FIG. 29, the stack St is subjected more or less to the full contact-pressure action. In the position according to FIG. 30, the spring spine 59 is being set back to an increasing extent into its precurved position, with the result that the stack St is relieved of the main pressure.

The installed parts are hidden from direct view as a result of the above-mentioned cover plate 58. The latter is only removed from its position in which it forms, as it were, a false floor when a new stack St of strip elements 4 is to be introduced.

Going beyond the function of contributing to the pocket formation 55, the cover plate 58 is also intended for the through-passage of the push rod 60 for actuating the spring 10. This is because the spine 59 of the spring 10, which is secured in a protected manner beneath the cover plate 58, is accessible via an opening 63. The latter is a longitudinal-slot-like through-passage which is of such a length that the spring 10 can also use the corresponding slot as a spring chamber; actuating play is provided.

Furthermore, the cover plate 58 has a viewing window 64 in the vicinity of the supply chamber 3, and also projecting away from the latter. This allows viewing in order to monitor the filling level of the dispenser 1. It is possible to see part of the strip-element stack St.

The end edge a of the cover plate 58, said edge being positioned in front of the viewing window 64, can, or is, also used here too in order to vary the discharging slot 15. It is set back in relation to the zone which is formed on the top side of the vertical surface of the wall 5, as boundary part b, by a good thickness of one strip element 4.

As far as the carrying ribs mentioned above in conjunction with the base grid 57 are concerned, it should also be pointed out that these are located such that the toothed bar 62 located in the U-space of the spring pusher 7, which is U-shaped in plan view, is well guided and supported on the base.

Following the base grid 57, provision is also made, in the base of the housing 6, for depressions 65 to the sides of the toothed bar 62. Said depressions accommodate drying-medium blocks 41.

The dispenser 1 is kept in the closed position via a closure tongue 66. The latter extends, in an integrally formed manner, from the border of the swing-action lid 26 on the longitudinal side which is directed away from the hinge joint 27. It (66) interacts with a mating latching surface 68. The latter is located at a congruent location on the underside of the base of the housing 6. The catch-type connection can be eliminated at will, with the result that the swing-action lid 26 is released in order to be transferred into the swing-open position.

Lateral guide ridges 69 serve for guidance and protection of the closure device 66/68.

Functioning is, briefly, as follows: with the closure device 66/68 being actuated with the effect of releasing the swing-action lid 26, the latter can be opened. This results in the first strip element 4' being lifted out and positioned obliquely. Said strip element is ultimately released and can easily be gripped by the sub-section 51 and drawn out of its friction-fitting retaining position. Removal takes place smoothly in respect of the clamping action on the sub-section 52, since the ratchet mechanism relieves pressure in this respect. It is only once the swing-action lid 26 has been closed that, via the spring 10, forward-moving, i.e. stack-shifting, advancement of the spring pusher 7 takes place. Positionally independent fixing of the stack St is then present; there are no play-utilizing displacements. Accordingly, the starting position according to FIG. 17, which allows easy gripping for the discharging pusher 14, is present such that it can always be reproduced precisely. The transfer into the closed position takes place with the pusher nose 16 being subjected to contact pressure and thus flattened.

The above type of construction manages with a very small number of components, that is to say the box-like housing 6 with film-hinge-secured swing-action lid 26, the spring pusher 7 and the cover plate 58, on which it is easily possible for the spring 10 to have already been integrally formed as a transporting finger. It is likewise possible for the elastically compliant pusher nose 16 to be already seated on the discharging pusher 14, assigned to the carrier 48 on the swing-action lid 26 by two-component injection molding. It is thus possible to manage with three parts.

I claim:

1. A dispenser (1) for dispensing strip elements (4), having a supply chamber (3) for accommodating a strip-element stack (St), and having a discharging pusher (14) with a nose (16) for interacting with a first strip element (4') of the strip-element stack (St), via a discharging slot (15) which is adapted to thickness (y) of a strip element (4), wherein the discharging pusher (14) has a pusher nose (16) which is made of elastically compliant material and, in the uninfluenced state, projects by more than the thickness (y) of the strip element (4).

2. The dispenser as claimed in claim 1, wherein, in an initial dispensing position, the pusher nose (16) projects such that it engages beneath the strip element (4'), which is ready for dispensing.

3. The dispenser as claimed in claim 1, wherein the pusher nose is shaped such that it projects in form of a wedge in direction of the strip element (4').

4. The dispenser as claimed in claim 1, wherein, the discharging pusher is coupled by a coupling to a swing-action lid (26) for pushing the discharging pusher (14) inward and drawing it outward, wherein the coupling (K) between the discharging pusher (14) and the swing-action lid (26) is operationally releasable.

5. The dispenser as claimed in claim 4, wherein, the swing-action lid (26) forms a downwardly projecting coupling part (28), and wherein the discharging slot (15) is formed between the coupling part (28) and a hinge joint (27) of the swing-action lid (26).

6. The dispenser as claimed in claim 5, wherein, at its free end, the coupling part (28) forms a latching head (29) which engages in an elongate hole (30) of the discharging pusher (14), with a longitudinal axis of the elongate hole (30) extending in direction of the hinge joint (27).

7. The dispenser as claimed in claim 5, wherein, the discharging pusher (14) is part of the swing-action dispenser lid (26), of which the hinge-joint axis of rotation (27) runs parallel to displacement direction (arrow z) of a spring pusher (7), the latter loading the strip-element stack in a dispensing direction.

8. The dispenser as claimed in claim 4, wherein, the axis of rotation of the hinge joint (27) of the swing-action lid (26) and a pivot axis (54) of the strip element (4') which is to be dispensed run parallel to one another, but at a distance apart, wherein, with the swing-action lid (26) closed, the pivot axis (54) of the strip element (4') is offset in direction of the discharging pusher (14), and at a lower level, relative to the axis of rotation of the hinge joint (27) of the swing-action lid (26).

9. The dispenser as claimed in claim 1, wherein, the discharging slot (is) is formed by interaction of an end surface (a) of a separately latchable bar part (35) with a housing-mounted boundary part.

10. The dispenser as claimed in claim 1, further comprising a spring pusher (7) loading the strip-element stack (St) in direction of a dispensing location of the strip element.

11. The dispenser as claimed in claim 10, wherein the discharging pusher is coupled by a coupling to a swing-action lid (26) for pushing the discharging pusher (14) inward and drawing it outward, the dispenser further comprising a housing (6) of the dispenser (1) said housing is formed with a viewing opening (36) and, under circumstances with the swing-action lid (26) open, allowing a visual check of the spring-pusher position.

12. The dispenser as claimed in claim 11, wherein, the viewing opening (36) is formed in a bar part (35).

13. The dispenser as claimed in claim 11, wherein, a visual marker (7") is integrally formed on the spring pusher (7), and wherein as a supply of strip elements decreases, said marker is displaced into a field of view of the viewing opening (36).

14. The dispenser as claimed in claim 10, wherein, the discharging pusher is coupled by a coupling to a swing-action lid (26) for pushing the discharging pusher (14) inward and drawing it outward, and wherein, the supply chamber (3) is combined with the spring pusher (7), the discharging pusher (14), the discharging slot (15) assigned to the supply chamber (3), and a chamber (40) provided with a hygroscopic material, to form a magazine (M) which is insertable from beneath into a housing (6) of the dispenser (1), on which the swing-action lid (26) is integrally formed.

15. The dispenser as claimed in claim 10, wherein, the spring pusher (7) is subjected to action of a spring (10) which acts with variable spring force.

16. The dispenser as claimed in claim 15, wherein, the spring force is reduced when the strip element (4') is pivoted out.

17. The dispenser as claimed in claim 15, wherein the discharging pusher is coupled by a coupling to a swing-action lid (26) for pushing the discharging pusher (14) inward and drawing it outward, wherein, the spring force is varied by the swing-action lid (26), which acts on a pre-curved spring spine (59), in dependence on position of the swing-action lid (26).

18. The dispenser as claimed in claim 17, further comprising a push rod (60) which acts on the spring spine (59) is formed on an inside of the swing-action lid (26).

19. The dispenser as claimed in claim 17, further comprising a cover plate (58) covering the strip-element stack (St) and the spring (10), the cover plate (58) having an opening (63) assigned to the spring spine (59).

20. The dispenser as claimed in claim 19, the cover plate (58) has a viewing window (64) which releases part of the strip-element stack (St).

21. The dispenser as claimed in claim 15, wherein, a free end of the spring (10) interacts in manner of a ratchet with a toothed bar (62) of the spring pusher (7).

22. The dispenser as claimed in claim 1, further comprising means for pivoting, a strip element (4) into a ready-for-removal position for dispensing.

23. The dispenser as claimed in claim 1, wherein, the pusher nose (16) only releases the first strip element (4'), which is ready for dispensing, once a sub-section (51) of the strip element (4) has been pivoted fully out of a surface of projection of the strip-element stack (St).

24. The dispenser as claimed in claim 23, wherein, the first strip element (4'), which is ready for dispensing, is exposed in said sub-section (51) which interacts with the discharging pusher (14).

25. The dispenser as claimed in claim 1, further comprising a housing (6), and wherein, a wall (5) of the housing (6) is of friction-enhanced form on a side directed toward the strip-element stack (St).

26. The dispenser as claimed in claim 25, wherein, said side of the wall (5) which is directed toward the strip-element stack (St) is rubber-coated.

27. The dispenser as claimed in claim 25, wherein, said wall (5) only extends over part of the length of the strip-element stack (St).

* * * * *

UNITED STATES PATENT AND TRADEMARK OFFICE
CERTIFICATE OF CORRECTION

PATENT NO. : 6,508,380 B1
DATED : January 21, 2003
INVENTOR(S) : Alfred von Schuckmann It is certified that error appears in the above-identified patent and that said Letters Patent is hereby corrected as shown below:

<u>Title page,</u>
Change Item "[22] Filed: Aug. 15, 2001" to -- PCT Filed: December 14, 2000 --
Insert items -- [86] PCT No.: PCT/EP00/12715 §371 (c)(1), (2), (4) Date: August 15, 2001 --; and
[87] PCT Pub. No.: WO 01/47786 PCT Pub. Date: July 5, 2001 --

Signed and Sealed this

Twenty-seventh Day of January, 2004

JON W. DUDAS
*Acting Director of the United States Patent and Trademark Office*